United States Patent
Eichler et al.

(10) Patent No.: US 10,546,396 B2
(45) Date of Patent: Jan. 28, 2020

(54) SYSTEM AND METHOD FOR REGISTRATION OF FLUOROSCOPIC IMAGES IN A COORDINATE SYSTEM OF A MEDICAL SYSTEM

(75) Inventors: Uzi Eichler, Haifa (IL); Yuval Vaknin, Hanaton (IL); Alon Izmirli, Ganot Hadar (IL); Shlomo Hoory, Givaat Ada (IL)

(73) Assignee: St. Jude Medical International Holding S.à r. l., Luxembourg (LU)

( * ) Notice: Subject to any disclaimer, the term of this patent is extended or adjusted under 35 U.S.C. 154(b) by 681 days.

(21) Appl. No.: 13/977,438

(22) PCT Filed: Dec. 25, 2011

(86) PCT No.: PCT/IB2011/055954
§ 371 (c)(1),
(2), (4) Date: Jun. 28, 2013

(87) PCT Pub. No.: WO2012/090148
PCT Pub. Date: Jul. 5, 2012

(65) Prior Publication Data
US 2013/0272592 A1    Oct. 17, 2013

Related U.S. Application Data

(60) Provisional application No. 61/428,440, filed on Dec. 30, 2010.

(51) Int. Cl.
*G06T 11/00* (2006.01)
(52) U.S. Cl.
CPC .................. *G06T 11/005* (2013.01)
(58) Field of Classification Search
CPC .... A61B 2034/2051; A61B 2090/3966; A61B 2034/2065; A61B 2090/364; G06T 2207/10121; G06T 7/30–38
(Continued)

(56) References Cited

U.S. PATENT DOCUMENTS

| 5,391,199 A | 2/1995 | Ben-Haim |
| 5,443,489 A | 8/1995 | Ben-Haim |

(Continued)

FOREIGN PATENT DOCUMENTS

| EP | 1942662 | 7/2008 |
| EP | 2722018 A2 | 4/2014 |

OTHER PUBLICATIONS

Mateen, Mala. "How to make a Motorized Linear Translation Stage." (2009).*

(Continued)

*Primary Examiner* — Wesley J Tucker
(74) *Attorney, Agent, or Firm* — Dykema Gossett PLLC

(57) ABSTRACT

A system for registering a group of images of an anatomical region of a patient in a coordinate system of a medical system is disclosed. The system includes an object disposed in a known position in the coordinate system. In one embodiment, the object has a first state in which the object is visible in at least one image and a second state in which the object is invisible in at least another image. In another embodiment, the object is substantially invisible to the eye in each image, but detectable by image processing. The system includes an electronic control unit configured to process the images to identify an image location of the object, create a transformation model responsive to the image location and the known position of the object in the coordinate system, and register the group of images in the coordinate system using the model.

8 Claims, 6 Drawing Sheets

(58) Field of Classification Search
USPC .................................................. 382/294, 132
See application file for complete search history.

(56) References Cited

U.S. PATENT DOCUMENTS

| | | | |
|---|---|---|---|
| 5,469,847 A * | 11/1995 | Zinreich | H05G 1/26 156/145 |
| 5,558,091 A | 9/1996 | Acker et al. | |
| 6,233,476 B1 | 5/2001 | Strommer et al. | |
| 6,498,944 B1 | 12/2002 | Ben-Haim et al. | |
| 6,567,689 B2 * | 5/2003 | Burbank | A61M 37/0069 600/420 |
| 6,690,963 B2 | 2/2004 | Ben-Haim et al. | |
| 6,788,967 B2 | 9/2004 | Ben-Haim et al. | |
| 7,139,418 B2 * | 11/2006 | Abovitz | A61B 6/12 382/132 |
| 7,197,354 B2 | 3/2007 | Sobe | |
| 7,386,339 B2 | 6/2008 | Strommer et al. | |
| 7,697,973 B2 | 4/2010 | Strommer et al. | |
| 2001/0044578 A1 * | 11/2001 | Ben-Haim | A61B 90/36 600/424 |
| 2003/0059097 A1 * | 3/2003 | Abovitz | A61B 6/12 382/132 |
| 2003/0130576 A1 * | 7/2003 | Seeley | A61B 6/12 600/426 |
| 2003/0179856 A1 | 9/2003 | Mitschke et al. | |
| 2005/0027193 A1 * | 2/2005 | Mitschke | G06T 7/0028 600/427 |
| 2005/0078802 A1 * | 4/2005 | Lang | A61B 6/505 378/207 |
| 2005/0085720 A1 * | 4/2005 | Jascob | A61B 5/06 600/424 |
| 2005/0085793 A1 * | 4/2005 | Glossop | A61B 90/36 604/529 |
| 2005/0281385 A1 | 12/2005 | Johnson et al. | |
| 2006/0115054 A1 | 6/2006 | Yatsenko et al. | |
| 2008/0009718 A1 * | 1/2008 | Zohman | A61B 19/54 600/426 |
| 2008/0097186 A1 * | 4/2008 | Biglieri | A61B 5/055 600/407 |
| 2008/0118115 A1 * | 5/2008 | Williamson | G06T 15/00 382/128 |
| 2008/0161682 A1 * | 7/2008 | Kendrick | A61B 19/5244 600/424 |
| 2010/0010341 A1 * | 1/2010 | Talpade | A61B 19/54 600/431 |
| 2012/0010503 A1 * | 1/2012 | Mangiardi | A61M 25/0108 600/435 |
| 2014/0114173 A1 * | 4/2014 | Bar-Tal | A61B 5/0035 600/409 |
| 2017/0014114 A1 * | 1/2017 | Rafiee | A61B 17/0057 |

OTHER PUBLICATIONS

"Medical Definition of Radiopaque." MedicineNet. www.medicinenet. corn/script/main/art.asp?articlekey=12057. Accessed Nov. 29, 2018. (Year: 2018).*

Author: , Title: International Search Report and Written Opinion Citation: PCT/IB2011/055954 dated Mar. 28, 2012.

* cited by examiner

SYSTEM AND METHOD FOR REGISTRATION OF FLUOROSCOPIC IMAGES IN A COORDINATE SYSTEM OF A MEDICAL SYSTEM

BACKGROUND OF THE INVENTION a. Field of the Invention

This invention relates to medical systems such as medical device navigation systems. Specifically, the instant invention relates to a system for registering a group of images of an anatomical region of a patient in a coordinate system of a medical system such as a medical device navigation system.

b. Background Art

It is desirable to track the position of medical devices as they are moved within a body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and clinician to undesirable levels of electromagnetic radiation. As a result, medical device navigation systems have been developed to track the position of medical devices within the body. These systems typically rely on the generation of electrical or magnetic fields and the detection of induced voltages and currents on position sensors attached to the medical device and/or external to the body. The information derived from these systems is then provided to a clinician through, for example, a visual display. Oftentimes, a representation of the medical device is displayed relative to a computer model or one or more images (including, but not limited to, fluoroscopic images) of the anatomical region in which the device is being maneuvered. In order to display the medical device at the correct location relative to the model or image, the model or image must be registered within the coordinate system of the navigation system.

Images may be registered in the coordinate system of a medical device navigation system in a variety of ways. If the imaging system used to capture the images is physically integrated with the navigation system, as described in commonly assigned U.S. patent application Ser. No. 11/971,004, the entire disclosure of which is incorporated herein by reference, the imaging system can be registered with the navigation system during installation and the spatial relationship of the navigation system to the imaging system is thereafter constant and known, obviating the need for registration during each new procedure. Where the navigation system and imaging system are physically separate, however, the changing spatial relationship of the systems makes registration more complicated. One solution is to place a plurality of radiopaque fiducial markers in the field of view of the imaging system at locations known relative to the coordinate system of the navigation system. Because the markers are visible in images produced by the imaging system, the images can be registered with the coordinate system by reconciling the visible location of each marker in the images with that marker's known location in the navigation coordinate system. One drawback to this solution, however, is that the fiducial markers are typically visible in the images seen by the clinician performing the procedure, potentially interfering with the clinician's view of the anatomical region being imaged.

The inventors herein have recognized a need for a system and method for registering a group of images of an anatomical region of a patient in a coordinate system of a medical device navigation system that will minimize and/or eliminate one or more of the above-identified deficiencies.

BRIEF SUMMARY OF THE INVENTION

It is desirable to provide a system and method for registering a group of images of an anatomical region of a patient in a coordinate system of a medical system such as a medical device navigation system.

A registration system for registering a group of images of an anatomical region of a patient in a coordinate system of a medical system in accordance with one embodiment of the invention includes an object, such as one or more fiducial markers, disposed in a known position in the coordinate system. The object is configured to assume a first state in which the object is visible in at least one image of the group of images and a second state in which the object is invisible in at least one other image of the group of images. The system further includes an electronic control unit configured to process the at least one image to identify an image location of the object in the at least one image. The electronic control unit is further configured to create a transformation model responsive to the image location of the object in the at least one image and the known position of the object in the coordinate system and register the group of images in the coordinate system using the transformation model. The electronic control unit may be further configured to superimpose an image of a medical device on each image of the group of images responsive to a position of the medical device within the coordinate system.

A method for registering a group of images of an anatomical region of a patient in a coordinate system of a medical system in accordance with one embodiment of the present invention includes a step of shifting an object, such as one or more fiducial markers, the object in a known position in the coordinate system, between a first state in which the object is visible in at least one image of the group of images and a second state in which the object is invisible in at least another image of the group of images. The method further includes the steps of processing the at least one image to identify an image location of the object in the at least one image and creating a transformation model responsive to the image location of the object in the at least one image and the known position of the object. The method further includes the step of registering the group of images in the coordinate system using the transformation model. The method may further include the step of superimposing an image of a medical device on each image of the group of images responsive to a position of the medical device within the coordinate system.

A registration system for registering a group of images of an anatomical region of a patient in a coordinate system of a medical system in accordance with another embodiment of the invention includes an electronic control unit configured to collect a plurality of images from the group of images, each of the plurality of images including a region containing an object. The object is in a known position in the coordinate system and substantially invisible to a human eye in each of the plurality of images. The control unit is further configured to determine an actual image location of the object in each of the plurality of images responsive to a summation of image data from each of the plurality of images. The image data identifies a potential image location for the object in each of the plurality of images. The control unit is further configured to create a transformation model responsive to the actual image location of the object in the plurality of images and the known position of the object and to register the group of images in the coordinate system using the transformation model.

A method for registering a group of images of an anatomical region of a patient in a coordinate system of a medical system in accordance with another embodiment of the present invention includes the step of collecting a plurality of images from the group of images, each of the plurality of images including a region containing an object. The object is in a known position in the coordinate system and substantially invisible to a human eye in each of the plurality of images. The method further includes the step of determining an actual image location of the object in each of the plurality of images responsive to a summation of image data from each of the plurality of images. The image data identifies a potential image location for the object in each of the plurality of images. The method further includes the steps of creating a transformation model responsive to the actual image location of the object in the plurality of images and the known position of the object and registering the group of images in the coordinate system using the transformation model.

A system and method in accordance with the present invention is advantageous because it allows images to be registered in the coordinate system of the physically separate medical system such as a medical device navigation system using objects such as fiducial markers without obscuring the imaged portions of the anatomical region or other items of interest in the image. As a result, the clinician is presented with a more accurate and detailed image of the anatomical region and related items of interest.

DETAILED DESCRIPTION OF THE DRAWINGS

One method of illustrating a medical device in an anatomical region of a patient is to superimpose a real-time rendered representation of the medical device on a group of images of the anatomical region. This method advantageously allows the clinician operating the medical device to view the device's location relative to the anatomical region without exposing the patient and clinician to excessive imaging radiation. The images are captured by an imaging system and a navigation system tracks the position of the medical device substantially in real time. A programmed electronic control unit creates a composite image for display comprising a representation of the tracked medical device superimposed on the group of images. To create the composite image, the images must first be registered in the coordinate system of the navigation system—i.e., the coordinate system of each image in the group must be reconciled with the coordinate system of the navigation system.

Figure 1:
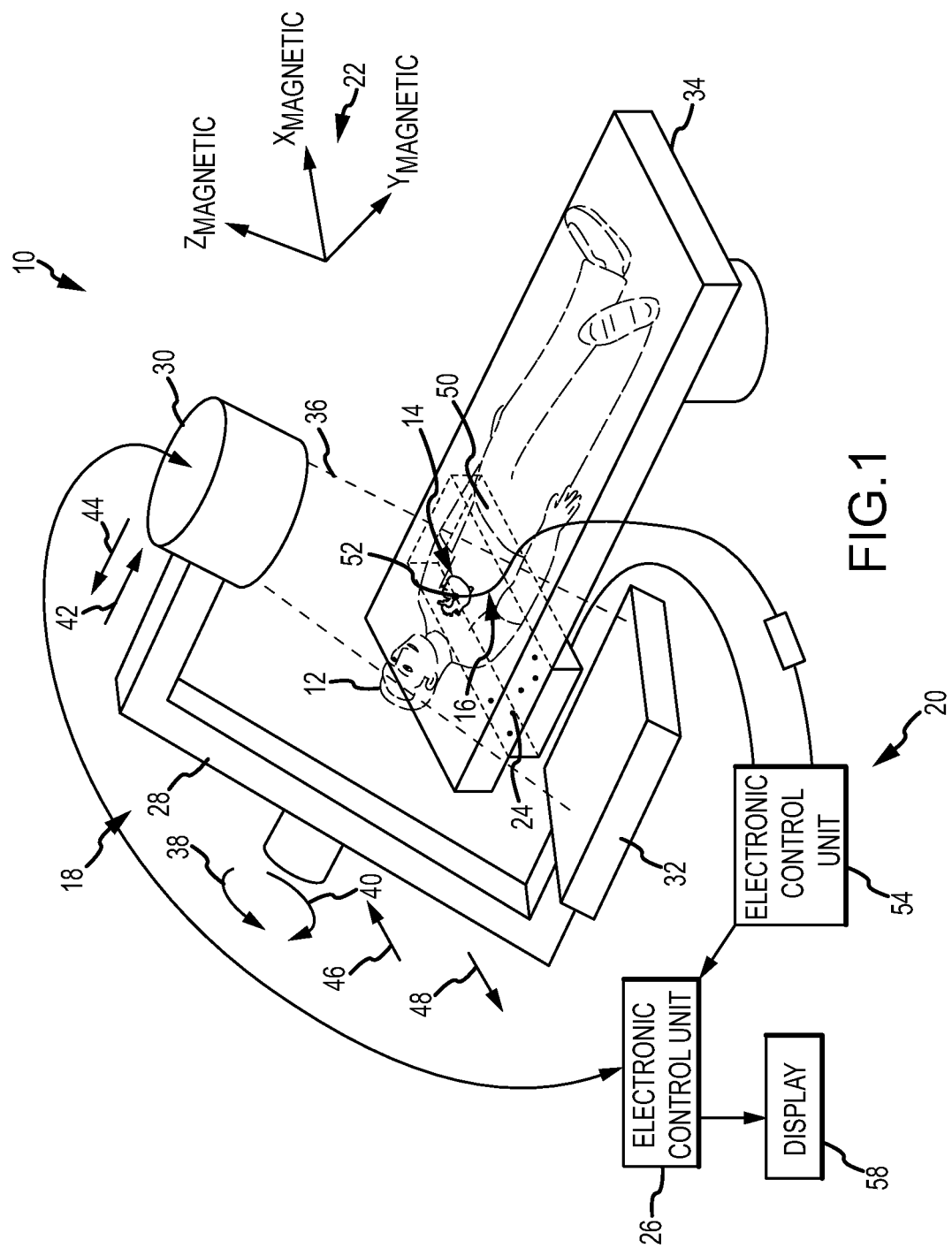
FIG. 1 is a diagrammatic view of one embodiment of a system for registering a group of images in a coordinate system of a medical system.

FIG. 1 illustrates an imaging and navigation system 10 for use in imaging an anatomical region of a patient 12 such as a heart 14 and for determining the position of, and navigating, a medical device 16 within the anatomical region. Device 16 may comprise, for example, an electrophysiological (EP) mapping catheter, an intracardiac echocardiography (ICE) catheter or an ablation catheter. It should be understood, however, that the inventive system could be used in imaging a variety of anatomical regions other than heart 14 and in connection with variety of diagnostic and treatment devices depending on the region of interest. System 10 includes an imaging system 18 and a medical device navigation system 20. In accordance with the present invention, system 10 also includes a registration system for registering a group of images of the anatomical region of patient 12 in a coordinate system 22 of navigation system 20. The registration system may include one or more objects 24 and an electronic control unit (ECU) 26.

Imaging system 18 is provided to acquire images of heart 14 or another anatomical region of interest and comprises a fluoroscopic imaging system in the illustrated embodiment. Although a fluoroscopic imaging system is described in this embodiment, the invention described herein may find use with other types of imaging systems configured to capture a group of images including, for example, but without limitation, computed tomography (CT) imaging systems and three-dimensional radio angiography (3DRA) systems. System 18 may include a C-arm support structure 28, a radiation emitter 30, and a radiation detector 32. Emitter 30 and detector 32 are disposed on opposite ends of support structure 22 and disposed on opposite sides of patient 12 as patient 12 lays on an operation table 34. Emitter 30 and detector 32 define a field of view 36 and are positioned such that the field of view 36 includes the anatomical region of interest as patient 12 lays on operation table 34. Imaging system 18 is configured to capture images of anatomical features and other objects within field of view 36. Support structure 28 may have freedom to rotate about the patient as shown by lines 38, 40. Support structure 28 may also have freedom to slide along lines 42, 44 (i.e. along the craniocaudal axis of patient 12) and/or along lines 46, 48 (i.e. perpendicular to the cranio-caudal axis of patient 12). Rotational and translational movement of support structure 28 yields corresponding rotational and translational movement of field of view 36.

Imaging system 18 may acquire a group of images of an anatomical region of patient 12 by first shifting along lines 42, 44, 46, 48 to place the anatomical region of interest within field of view 36. Second, support structure 28 may rotate radiation emitter 30 and radiation detector 32 about patient 12, keeping the anatomical region within field of view 36. Imaging system 18 may capture images of the anatomical region as support structure 28 rotates, providing a group of two-dimensional images of the anatomical region from a variety of angles. The group of images may be communicated to ECU 26 for image processing and display. The group of images may comprise a sequence of images taken over a predetermined time period.

Navigation system 20 is provided to determine the position of medical device 16 within the body of patient 12 and to permit a clinician to navigate device 16 within the body. In the illustrated embodiment, system 20 comprises a magnetic navigation system in which magnetic fields are generated in the anatomical region and position sensors associated with device 16 generate an output that changes responsive to the position of the sensors within the magnetic field. System 20 may comprise, for example, the system offered for sale under the trademark "GMPS" by Medi-Guide, Ltd. and generally shown and described in, for example, U.S. Pat. Nos. 6,233,476, 7,197,354 and 7,386,339, the entire disclosures of which are incorporated herein by reference or the system offered for sale under the trademark "CARTO XP" by Biosense Webster, Inc. and generally shown and described in, for example, U.S. Pat. Nos. 5,391,199, 5,443,489, 5,558,091, 6,498,944, 6,788,967 and 6,690,963, the entire disclosures of which are incorporated herein by reference. Although a magnetic navigation system is shown in the illustrated embodiment, it should be understood that the invention could find use with a variety of navigation systems including those based on the creation and detection of axes specific electric fields, such as the system offered for sale by St. Jude Medical, Inc. under the trademark "ENSITE NAVX." Navigation system 20 may include a transmitter assembly 50 and one or more position sensors 52 together with an electronic control unit (ECU) 54.

Transmitter assembly 50 is conventional in the art and may include a plurality of coils arranged orthogonally to one another to produce a magnetic field in and/or around the anatomical region of interest. It should be noted that, although transmitter assembly 50 is shown under the body of patient 12 and under table 34 in FIG. 1, transmitter assembly 50 may be placed in another location, such as attached to radiation emitter 30, from which the magnetic field generators can project a magnetic field in the anatomical region of interest. In accordance with certain embodiments of the invention transmitter assembly 50 is within field of view 36.

Position sensors 52 are configured to generate an output dependent on the relative position of sensors 52 within the field generated by transmitter assembly 50. Sensors 52 are in a known positional relationship to device 16 and may be attached to medical device 16. In FIG. 1, position sensor 52 and medical device 16 are shown disposed within the heart 14. Position sensors 52 may be attached to the distal or proximal end of device 16, or any point in between. As medical device 16 is guided to and through the anatomical region of interest, navigation system 20 determines the location of position sensors 52 in the generated field, and thus the position of medical device 16.

ECU 54 is provided to control the generation of magnetic fields by transmitter assembly 50 and to process information received from sensors 52. ECU 54 may comprise a programmable microprocessor or microcontroller or may comprise an application specific integrated circuit (ASIC). ECU 54 may include a central processing unit (CPU) and an input/output (I/O) interface through which ECU 54 may receive a plurality of input signals including signals generated by sensors 52 and generate a plurality of output signals including those used to control transmitter 50. Although ECU 54 is shown as a separate component in the illustrated embodiment, it should be understood that ECU 54 and ECU 26 could be integrated into a single unit.

Objects 24 are provided to permit registration of images captured by imaging system 18 in coordinate system 22 of navigation system 20. Each object 24 may comprise, for example, one or more fiducial markers. Objects 24 are within the field of view 36 of imaging system 18. Objects 24 are also either located at a known position within coordinate system 22 or are connected to a sensor that can provide a position within coordinate system 32. In the illustrated embodiment, for example, objects 24 are placed on a component of navigation system 20 that is within field of view 36, such as transmitter 50. Alternatively, objects 24 may be placed at a fixed distance from a component, e.g. transmitter 50, of system 20, but still within the field of view 36. Objects 24 may also be affixed to a distal end portion of a catheter that is disposed within field of view 36, or to a body portion of the patient within field of view 36. Alternatively, objects 24 may include a sensor (not shown) similar to sensor 52 that is locatable in navigation system 20. Objects 24 may remain in the same known position within coordinate system 22 over time or may move between different known positions in the coordinate system 22 (e.g., where a subsequent positions has a known relationship to a prior known position within coordinate system 22). In the case of an object 24 that includes a plurality of fiducial markers, the markers may be arranged in a predetermined pattern or otherwise in a manner where the markers have a known relationship to one another. The markers may also have different degrees of radiopacity.

In accordance with one embodiment of the present invention, objects 24 assume a first state in which objects 24 are visible in one or more of the group of images captured by imaging system 18 and a second state in which objects 24 are invisible in other images of the group of images captured by imaging system 18. As imaging system 18 acquires images of heart 14 or another anatomical region, objects 24 may switch between their first state and their second state. Thus, objects 24 may appear in at least one image of the group of images acquired by imaging system 18 (marked images), but may be invisible in at least one other image of the group of images (unmarked images).

Objects 24 can be switched between states in a variety of ways. In one embodiment, objects 24 comprise a material that changes between a radiopaque state in which objects 24 are visible in the captured images and a radiolucent state in which objects 24 are invisible in the captured images. The objects 24 may change between the two states in response to a variety of stimuli. For example, in one embodiment of the invention, objects 24 are made from a material that changes between the radiopaque and radiolucent states in response to exposure to electromagnetic radiation. In another embodiment, objects 24 are made from a material that changes between the radiopaque and radiolucent states in response to an electric signal from, for example, ECU 26. In yet another embodiment, objects 24 are made from a material that changes between the radiopaque and radiolucent states in the presence of a radiopaque dye introduced into the anatomical region of the patient. In any of these embodiments, the stimuli may cause objects 24 to move from the radiopaque state to the radiolucent state or from the radiolucent state to the radiopaque state depending on the material of objects 24. The change from one state to another state may be temporary and repeatable. Alternatively, the change in state may be permanent and unrepeatable. In practice, objects 24 may be radiopaque only at the start of a procedure, at various key stages of the procedure, or at regular intervals. Thus, the two systems may be registered once at the beginning of the procedure, at various stages, or near continuously depending on the needs of the clinician.

Figure 2:
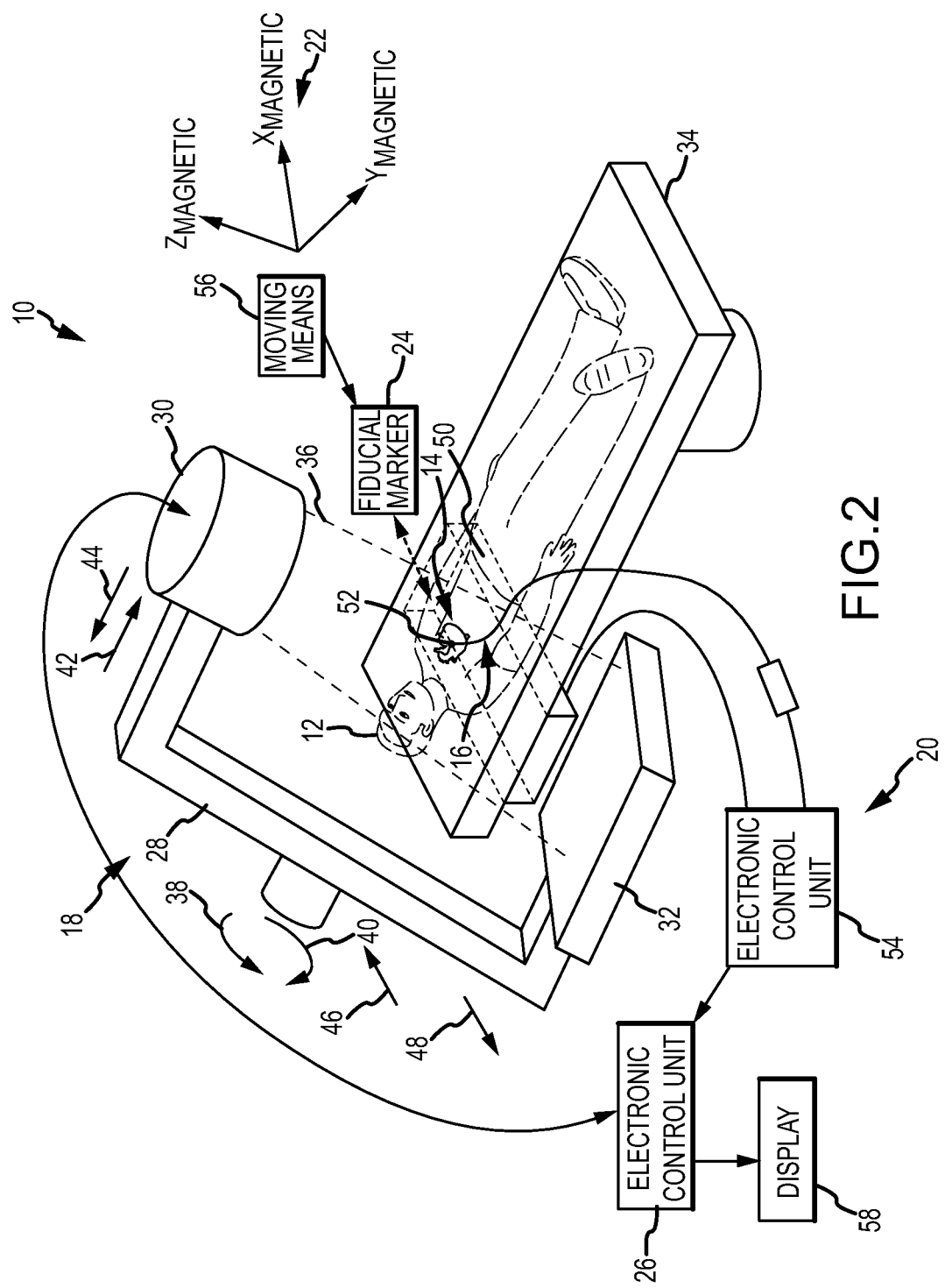
FIG. 2 is a diagrammatic view of another embodiment of a system for registering a group of images in a coordinate system of a medical system.

Referring to FIG. 2, in another embodiment of the invention, the registration system includes means 56 for moving objects 24 between a position disposed within the field of view 36 (such that objects 24 are in a first state and visible in images captured by imaging system 18) and another position disposed outside of field of view 36 (such that objects 24 are in a second state and invisible in images captured by imaging system 18). The moving means 56 may comprise any conventional mechanical apparatus that moves the objects 24 between positions by linear or rotational or other motion (e.g., a linear actuator or a motor driven table) operating under the control of ECU 26. In yet another embodiment of the invention, the registration system includes means, such as a radiopaque shield, for shielding objects 24 within field of view 36 such that objects 24 remain within field of view 36, but are invisible when the shielding means is disposed between emitter 30 of imaging system 18 and objects 24. The profile of the shielding means may be minimized to avoid obscuring anatomical features in the images.

In yet another embodiment of the invention, objects 24 are configured with a relatively low intensity and/or a relatively gradual variation in intensity such that objects 24 are substantially invisible to the human eye in the images generated by imaging system 18, but are detectable through image processing by ECU 26 as described hereinbelow. Objects 24 may, for example be relatively thin or may have a low, but existent, radiopacity. In one embodiment, objects 24 are made from an aluminum foil or aluminum sheet. It should be understood, however, that objects 24 may be made from a variety of metals, metal alloys or other materials having at least a minimal level of radiopacity. In another embodiment, the radiopacity of object 24 gradually increases or decreases moving from one point on object 24 to another point on object 24 (e.g., the radiopacity is greater near a center of an object 24, but gradually decreases moving away from the center of an object 24) taking advantage of the fact that the human eye has difficulty in detecting relatively small changes. Objects 24 may assume any of a variety of sizes and shapes.

Although multiple embodiments of objects 24 are described separately herein, it should be understood that multiple types of objects may be used in a single application and still fall within the scope of the present invention. For instance, but without limitation, objects 24 made from a material that changes between the radiopaque and radiolucent states in response to an electric signal may be used in conjunction with objects 24 that remain permanently in the radiopaque state. In another example, but without limitation, a first set of objects 24 may be moved in and out of field of view 36 by moving means 56, and a second set of objects 24 may be made from a material that changes between the radiopaque and radiolucent states in response to exposure to electromagnetic radiation. In yet another example, but without limitation, a first set of objects 24 may remain in a permanently radiopaque state in field of view 36, a second set of objects 24 may be made from a material that changes between the radiopaque and radiolucent states in the presence of a radiopaque dye introduced into the anatomical region of the patient, and a third set of objects 24 may be moved in and out of field of view 36 by moving means 56.

ECU 26 is provided for processing images generated by imaging system 18 and registering the images in coordinate system 22 based on the appearance of objects 24 in the images. ECU 26 may also control the operation of medical device 16, imaging system 18, navigation system 20 and/or a display 58. ECU 26 may comprise a programmable microprocessor or microcontroller or may comprise an application specific integrated circuit (ASIC). ECU 26 may include a central processing unit (CPU) and an input/output (I/O) interface through which ECU 26 may receive a plurality of input signals including signals generated by device 16, imaging system 18, and navigation system 20 and generate a plurality of output signals including those used to control device 16, imaging system 18, navigation system 20 and display 58. ECU 26 may also receive an input signal from an organ monitor (not shown), such as an ECG monitor, and sort or segregate images from imaging system 18 based on a timing signal of a monitored organ. For example, ECU 26 may sort images based on the phase of the patient's cardiac cycle at which each image was collected, as more fully described in commonly owned U.S. Pat. No. 7,697,973 to Strommer et al., which is hereby incorporated by reference in its entirety.

Figure 3:
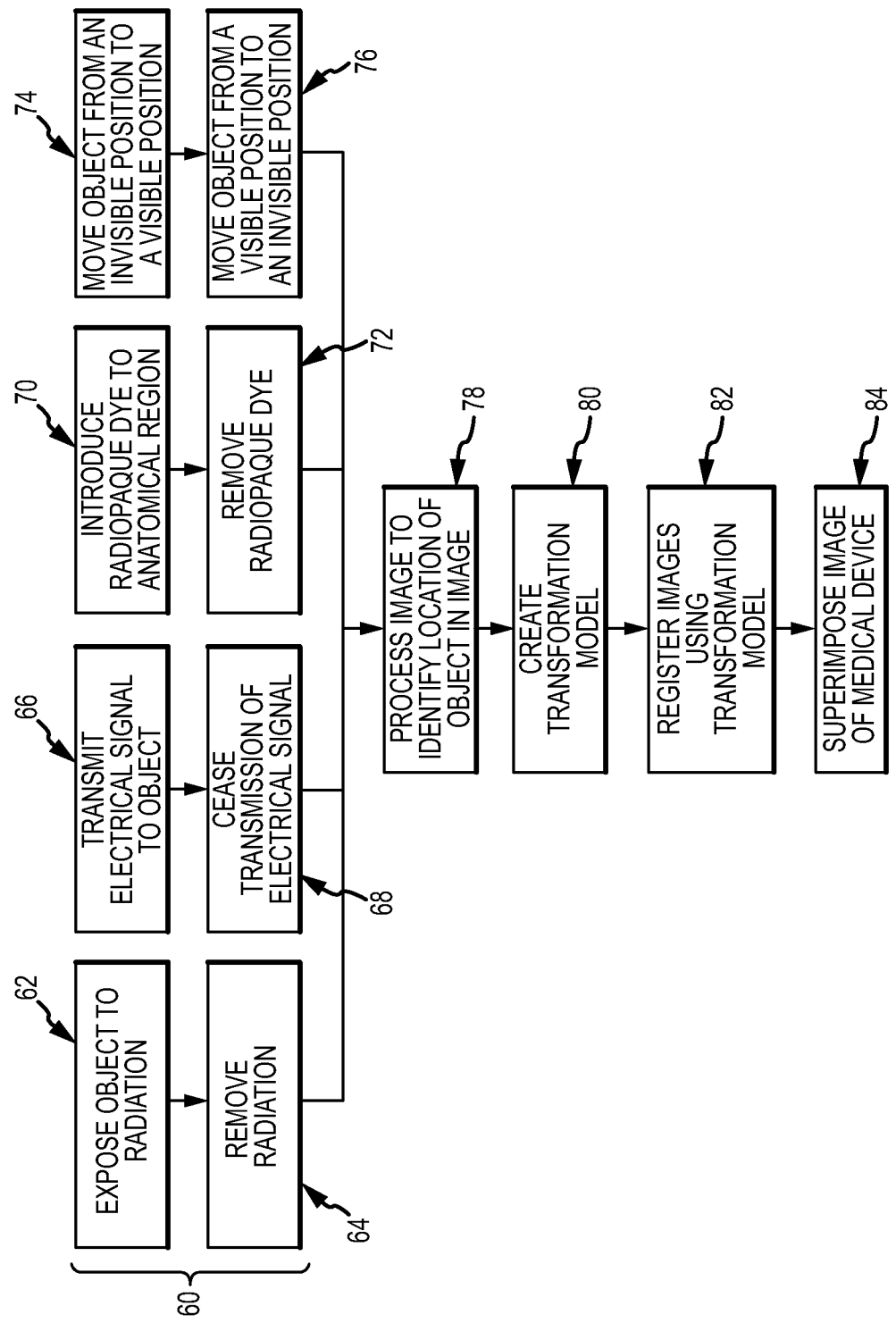
FIG. 3 is a flow chart diagram illustrating one embodiment of a method for registering a group of images in a coordinate system of a medical system.

In accordance with the present invention, ECU 26 is configured with appropriate programming instructions or code (i.e., software) to perform several steps in a method for registering a group of images of heart 14 or another anatomical region of patient 12 in coordinate system 22 of navigation system 20. Referring to FIG. 3, one embodiment of the inventive method may begin with the step 60 of shifting an object 24 between a first state in which the object 24 is visible in at least one image of the group of images and a second state in which the object 24 is invisible in at least another image of the group of images. As discussed hereinabove, this step may be performed in a variety of ways. In one embodiment of the inventive method, step 60 includes the substep 62 of exposing an object 24 to electromagnetic radiation. Step 60 may likewise include the substep 64 of concealing or removing the electromagnetic radiation such that object 24 is no longer exposed. These steps may be performed by imaging system 18 operating under the control of ECU 26. In another embodiment of the inventive method, step 60 includes the substep 66 of transmitting an electrical signal to object 24 to stimulate the change in state. Step 60 may likewise include the substep 68 of ceasing transmission of the electrical signal to allow object 24 to return to its original state. The electrical signal may be generated by ECU 26. In yet another embodiment of the inventive method, step 60 includes the substep 70 of introducing a radiopaque dye to the heart 14 or other anatomical region of patient 12 to stimulate the change in state of object 24. Note that wile the dye may have its own response to the radiation while in the heart 14, it is its use in or within object 24 that is the focus herein. Step 60 may likewise include the substep 72 of removing the radiopaque dye from the anatomical region (e.g. by flushing the region with fluid). In yet another alternative embodiment, step 60 may include the substeps 74, 76 of moving object 24 between positions disposed outside of field of view 36 to a position within field of view 36. The movement of objects 24 may be under the control of ECU 26.

Although a variety of methods for step 60—shifting a object 24 between a first state in which the object 24 is visible in at least one image of the group of images and a second state in which the object 24 is invisible in at least another image of the group of images—are illustrated in the alternative, it should be understood that two or more such methods could be performed in a single application and still fall within the scope of the present invention. For example, but without limitation, substeps 66 (transmitting an electrical signal to a first object 24) and 68 (ceasing transmission of the electrical signal) could be performed in conjunction with substeps 74 (moving a second object 24 from an invisible position to a visible position) and 76 (moving the second object from the visible position to the invisible position).

The method may further include the step 78 of processing the image or images in which the object 24 is visible to identify an image location of the object 24 in the images. ECU 26 may perform this function using conventional image processing algorithms to identify the objects 24 in the images. The method further includes the step 80 of creating a transformation model responsive to the image location of the object 24 in the image or images and the known position of object 24 in coordinate system 22. As discussed above, objects 24 are disposed in a known position within coordinate system 22, this known position being determined before step 80. In particular, objects 24 may be affixed to a component of navigation system 20 such as transmitter 50 or may be positioned at a fixed distance from such a component. Knowing the position of object 24 within coordinate system 22 and the position of object 24 within the image, ECU 26 can create a transformation model in a conventional manner to allow registration of the group of images including those images in which the object 24 is invisible. The method may further include the step 82 of registering the group of images in coordinate system 22 using the transformation model. Finally, the method may include the step 84 of superimposing an image of device 16 on each image in the group of images responsive to the position of device 16 within coordinate system 22. Once the group of images is registered within coordinate system 22, ECU 26 generates image data combining each image in the group with a representation of device 16. Because both the images and device 16 are registered within coordinate system 22, an accurate representation of the position of device 16 relative to the anatomical features shown in the images can be displayed on display 58.

Figure 4A:
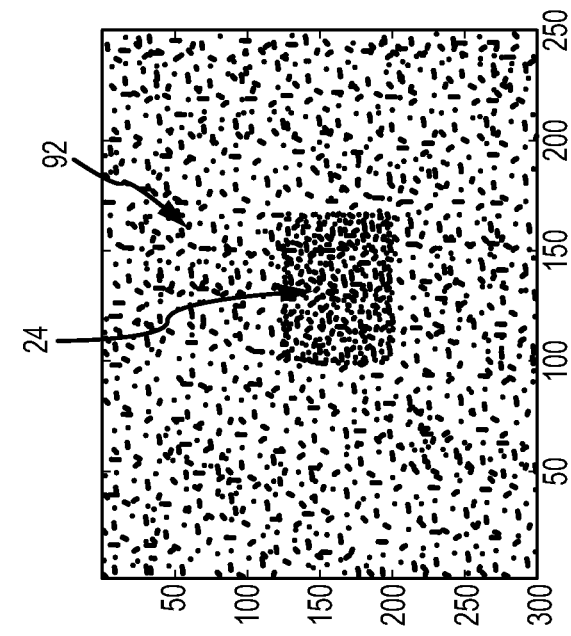
FIGS. 4A-B are diagrammatic representations of an image containing an object generated by an imaging system and a processed image generated by an electronic control unit integrating a plurality of such images.
Figure 4B:
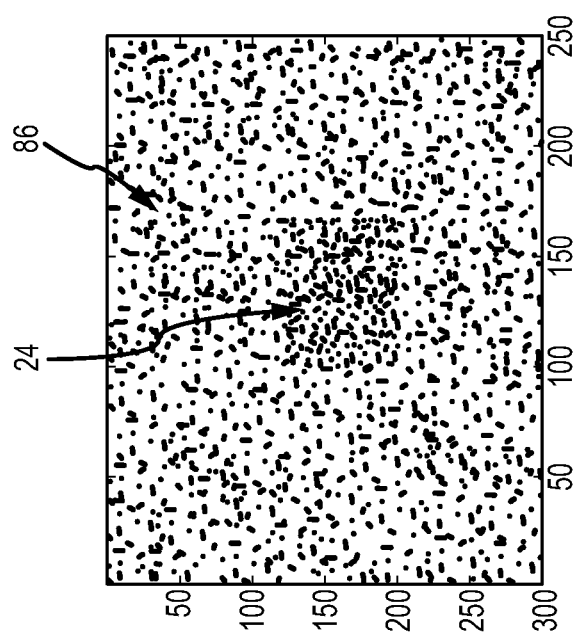
Figure 5:
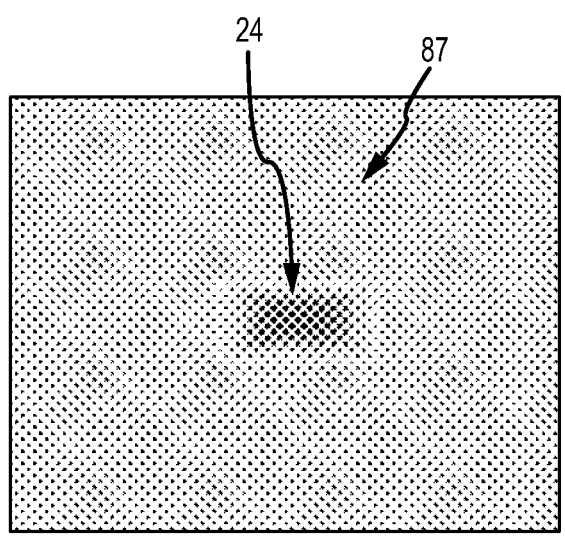
FIG. 5 is a diagrammatic representation of another image containing an object generated by an imaging system for processing by an electronic control unit integrating a plurality of such images.
Figure 6:
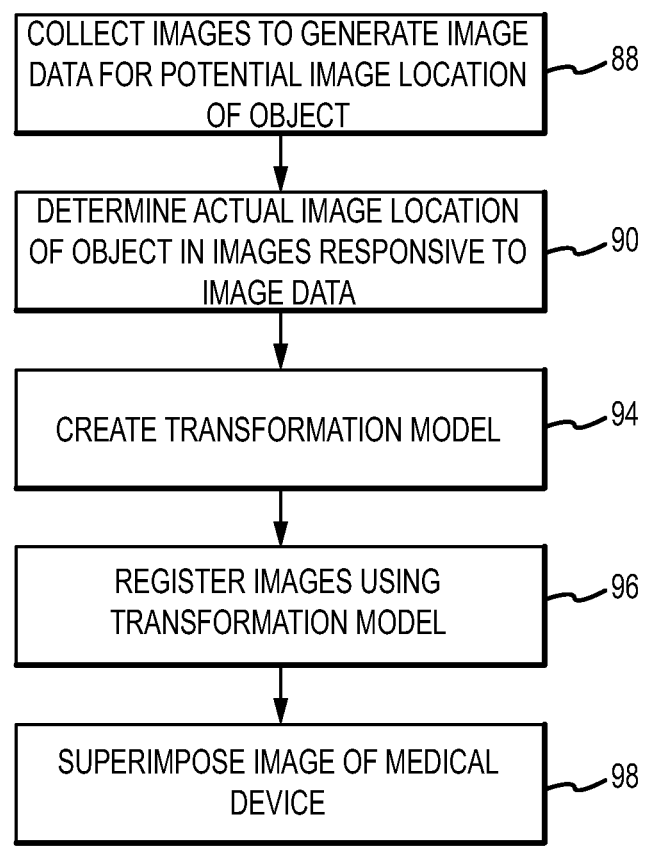
FIG. 6 is flow chart diagram illustrating another embodiment of a method for registering a group of images in a coordinate system of a medical system.

As discussed hereinabove, in another embodiment of the invention, objects 24 are configured with a relatively low intensity and/or a relatively gradual variation in intensity such that objects 24 are substantially invisible to the human eye in the images generated by imaging system 18, but are detectable through image processing by ECU 26. Referring to FIG. 4A, one exemplary image 86 taken by imaging system 18 is shown that includes a relatively obscure object 24. Referring to FIG. 5, another exemplary image 87 includes an object 24 having a gradual variation in intensity in which the radiopacity of object 24 gradually decreases moving outward from the center of object 24. Referring now to FIG. 6, another embodiment of the inventive method may therefore begin with the step 88 of collecting a plurality of images 86 or 87 from the group of images generated by imaging system 18 wherein each of the collected images includes a region containing an object 24 that is in a known position in coordinate system 22, but is substantially invisible to the human eye. Depending on the intensity of the objects 24 and the processing capabilities of ECU 26, the plurality of images 86 or 87 collected by ECU 26 may comprise the entire group of images or a subset of the group of images. The method may continue with the step 90 of determining an actual image location for object 24 in each of the images responsive to a summation of image data from each image, the image data identifying a potential image location for object 24 in each of the images. ECU 26 may use conventional algorithms in summation of the image data including summing and/or averaging the data in order to eliminate noise in the data and determine the actual image location of object 24 in each of the plurality of images 86 or 87. Referring to FIG. 4B, for example, a processed image 92 is shown resulting from an integration of the data obtained from images 86. In image 92, the location of object 24 is more clearly shown than in any of images 86. In processing the data, ECU 26 may use all of the data or a subset of the data. For example, ECU 26 may determine that data obtained from one or more images is unreliable in view of one or more characteristics of the data (including variances from data obtained from other images) and discard such data. ECU 26 may also be able to determine the actual location of object 24 based on data from a subset of the plurality of images and terminate further processing. The method may continue with the step 94 of creating a transformation model responsive to the actual image location of the object 24 in the plurality of images and the known position of the object 24 in the coordinate system 22, the step 96 of registering the group of images in coordinate system 22 using the transformation model, and the step 98 of superimposing an image of device 16 on each image in the group of images responsive to the position of device 16 within coordinate system 22. Steps 94, 96, 98 are substantially similar to steps 80, 82, 84 and, therefore, a further description of steps 94, 96, 98 may therefore be found hereinabove.

A system and method for registering a group of images of an anatomical region of a patient 12 in a coordinate system 22 of medical system such as medical device navigation system 20 in accordance with the present invention represents an improvement over conventional systems. Using the inventive system and method, a clinician can guide and operate device 16 to and within the anatomical region while viewing a representation of the device 16 relative to actual images of the anatomical region. Because the group of images is pre-acquired, the clinician and patient 12 are not exposed to excessive doses of imaging radiation during the procedure. Further, because the objects 24 are substantially invisible in the acquired images or visible in only some of the acquired images, the objects do not impede the clinician's view of anatomical region 12.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily imply that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims

What is claimed is:

1. A coordinate system registration system, comprising:
   radiopaque elements arranged in a fixed predetermined pattern within a registration module and configured, in response to the radiopaque elements generating a fluoroscopic image, to define a position of the module in a fluoroscopic coordinate system of reference; and
   a magnetic field transmission pad;
   wherein the module is located outside of and detached from a patient's body at a fixed distance from the magnetic field transmission pad at a predetermined location with respect to the pad, so as to characterize the position of the registration module in a magnetic coordinate system of reference defined by the magnetic field transmission pad;

wherein the radiopaque elements are configured to assume a first state in which each of the radiopaque elements is visible and a second state in which each of the radiopaque elements is invisible; and wherein the radiopaque elements are configured to assume the first state upon exposure to at least one of electromagnetic radiation or radiopaque dye, and wherein the radiopaque elements are configured to assume the second state upon removal of the at least one of electromagnetic radiation or radiopaque dye.

2. A method for registering coordinate systems, comprising:

arranging radiopaque elements in a fixed predetermined pattern within a registration module;

generating a fluoroscopic image of the radiopaque elements;

evaluating a fluoroscopic position of the registration module in a fluoroscopic coordinate system of reference in response to the fluoroscopic image;

positioning the registration module outside of and detached from a patient's body at a fixed distance from a magnetic field transmission pad and at a predetermined location and orientation with respect to the pad, so as to characterize a magnetic position of the registration module in a magnetic coordinate system of reference defined by the magnetic field transmission pad; and registering the fluoroscopic coordinate system with the magnetic coordinate system by equating the fluoroscopic position of the registration module with the magnetic position of the registration module;

wherein the radiopaque elements are configured to assume a first state in which each of the radiopaque elements is visible and a second state in which each of the radiopaque elements is invisible; and wherein the radiopaque elements are configured to assume the first state upon exposure to at least one of electromagnetic radiation or radiopaque dye, and wherein the radiopaque elements are configured to assume the second state upon removal of the at least one of electromagnetic radiation or radiopaque dye.

3. The method according to claim 2, wherein registering the coordinate systems comprises creating a transformation model.

4. The method according to claim 3, wherein registering the coordinate systems comprises registering a group of fluoroscopic images with the magnetic coordinate system using the transformation model.

5. The method according to claim 4, further comprising superimposing a representation of a medical device on each image within the group of fluoroscopic images responsive to a position of the medical device within the magnetic coordinate system.

6. The registration system of claim 1, wherein the radiopaque elements are configured to assume the first state in a first fluoroscopic image and the second state in a second fluoroscopic image.

7. The method of claim 2, wherein the generating step further comprises generating a first fluoroscopic image and generating a second fluoroscopic image; wherein the radiopaque elements are configured to assume the first state in the first fluoroscopic image and the second state in the second fluoroscopic image; and wherein the evaluating step further comprises evaluating the fluoroscopic position of the registration module in the fluoroscopic coordinate system of reference in response to the first fluoroscopic image.

8. The method of claim 7, wherein the registering step further comprises registering the second fluoroscopic image with the magnetic coordinate system.

* * * * *